(12) United States Patent
Arnatt et al.

(10) Patent No.: US 9,951,271 B2
(45) Date of Patent: Apr. 24, 2018

(54) PROCESS FOR MAKING AN ASYMMETRIC FLUOROPHORE

(71) Applicant: UNITED STATES OF AMERICA, AS REPRESENTED BY THE SECRETARY OF COMMERCE, Washington, DC (US)

(72) Inventors: Christopher Arnatt, Kirkwood, MO (US); John Elliott, Silver Spring, MD (US)

(73) Assignee: THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 0 days.

(21) Appl. No.: 15/294,065

(22) Filed: Oct. 14, 2016

(65) Prior Publication Data

US 2017/0121599 A1    May 4, 2017

Related U.S. Application Data

(60) Provisional application No. 62/249,429, filed on Nov. 2, 2015.

(51) Int. Cl.
*C09K 11/06* (2006.01)
*G01N 1/30* (2006.01)
*C07F 5/02* (2006.01)

(52) U.S. Cl.
CPC .............. *C09K 11/06* (2013.01); *C07F 5/022* (2013.01); *G01N 1/30* (2013.01); *C09K 2211/1029* (2013.01); *G01N 2001/302* (2013.01)

(58) Field of Classification Search
CPC ............ C09K 11/06; C07F 5/022; C01N 1/30
USPC ............................................................ 544/1
See application file for complete search history.

(56) References Cited

U.S. PATENT DOCUMENTS 4,774,339 A    9/1988    Haugland et al.

OTHER PUBLICATIONS

Mempel, T.R., et al., Regulatory T-cell reversibly suppress cytotoxic T-cell function independent of effector differentiation, Immunity, 2006, 129-141, 25.
Marques, I.J., et al., Metastatic behaviour of primary human tumors in a zebrafish xenotranplantation model, BMC Cancer, 2009.
Watanabe, K., et al., In vivo imaging of zebrafish retinal cells using fluorescent coumarin derivatives, BMC Neuroscience, 2010.
Elliott, J.T., et al., Comparison of reagents for shape analysis of fixed cells by automated fluorescence microscopy, Cytometry Part A, 2003, 90-100.
Parish, C.R., Fluorescent dyes for lymphocyte migration and proliferation studies, Immunology and cell biology, 1999, 499-508, 77.

*Primary Examiner* — Kahsay Habte
(74) *Attorney, Agent, or Firm* — Toby D. Hain

(57) ABSTRACT

The present invention relates to a process for making an asymmetric fluorophore. The asymmetric fluorophore is useful as a stain for staining live cells or fixed cell and provides whole-cell staining of such cells.

7 Claims, 16 Drawing Sheets

PROCESS FOR MAKING AN ASYMMETRIC FLUOROPHORE

CROSS REFERENCE TO RELATED APPLICATIONS

This application claims the benefit of U.S. Provisional Patent Application Ser. No. 62/249,429, filed Nov. 2, 2015, the disclosure of which is incorporated herein by reference in its entirety.

STATEMENT REGARDING FEDERALLY SPONSORED RESEARCH

This invention was made with United States Government support from the National Institute of Standards and Technology. The Government has certain rights in the invention.

BRIEF DESCRIPTION

Disclosed is a process for making an asymmetric fluorophore, the process comprising: decarboxylating a compound of formula 1

Formula 1 to form a compound of formula 2

Formula 2 condensing the compound of formula 2 with 2-pyrrole aldehyde to form a compound of formula 3

Formula 3 difluorinating the compound of formula 3 in a presence of boron trifluoride ethyl etherate to form a compound of formula 4

Formula 4 hydrolyzing the compound of formula 4 to form a compound of formula 5

Formula 5 and succinimating the compound of formula 5 to form the asymmetric fluorophore comprising a compound of formula 6

Formula 6

Also disclosed is a process for whole-cell staining, the process comprising: decarboxylating a compound of formula 1

Formula 1 to form a compound of formula 2

Formula 2 converting the compound of formula 2 to form the asymmetric fluorophore comprising a compound of formula 6

Formula 6

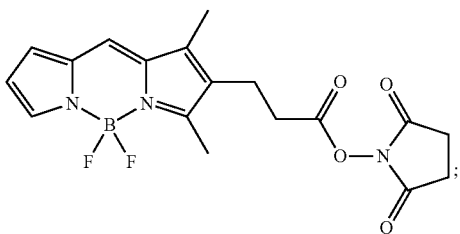

combining the asymmetric fluorophore and a cell; and forming a radical of formula 7

Formula 7

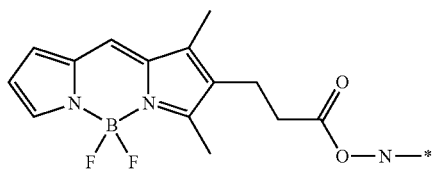

by reacting the asymmetric fluorophore with a primary amine in a cellular compound from the cell to irreversibly couple the radical of formula 7 to the cellular compound to stain the cell with the radical of formula 7 and to form a stained cellular compound having an amide linkage between the radical of formula 7 and the cellular compound, the cellular compound being a component of the cell prior to staining the cell with the radical of formula 7, wherein the stained cellular compound remains a part of the cell after staining the cell with the asymmetric fluorophore.

BRIEF DESCRIPTION OF THE DRAWINGS

The following descriptions should not be considered limiting in any way. With reference to the accompanying drawings, like elements are numbered alike.

DETAILED DESCRIPTION

Figure 1:
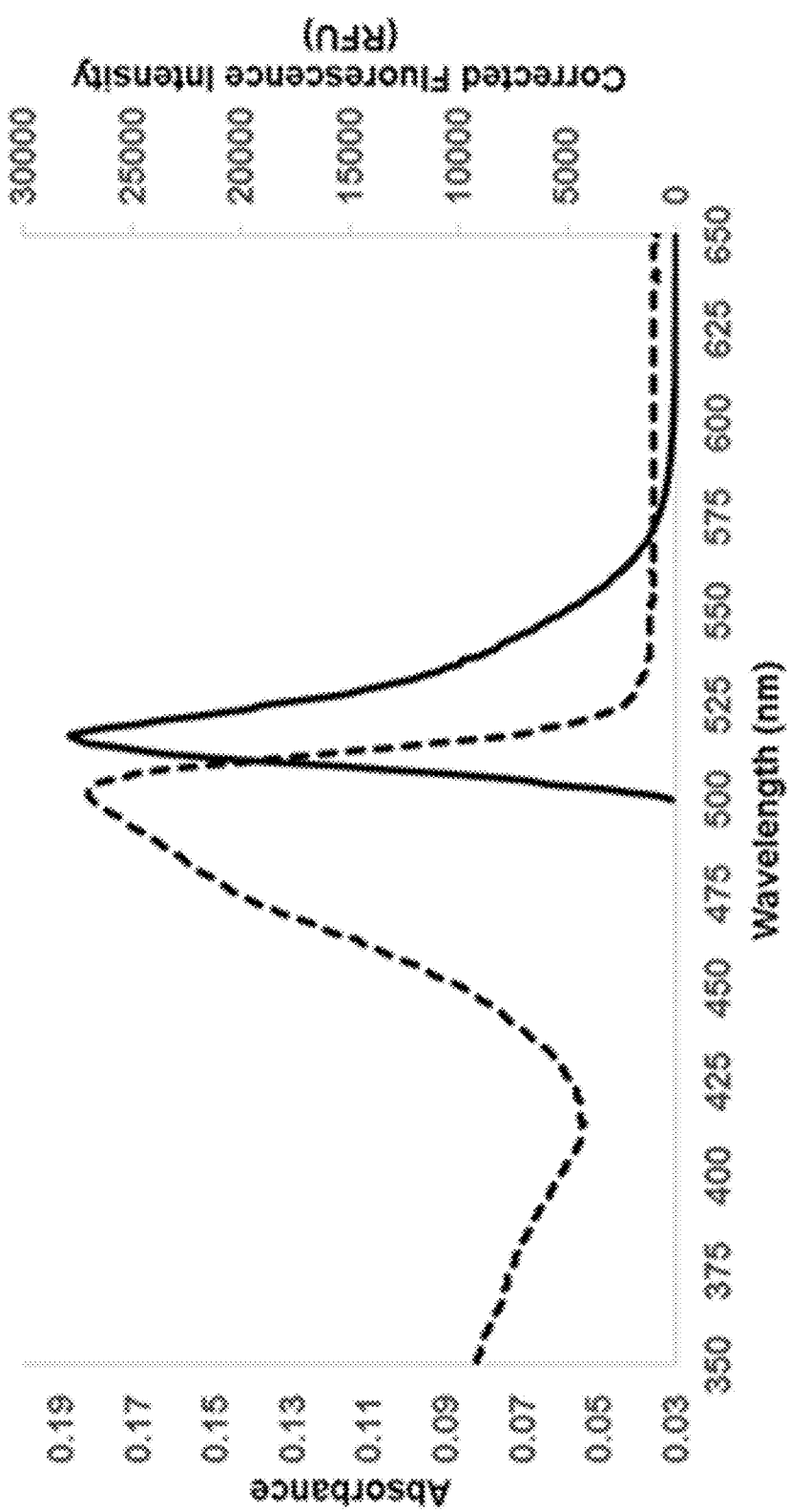
FIG. 1 shows excitation and emission spectra of an asymmetric fluorophore in water (10% MeOH). Fluorescence spectra corrected using NIST SRM 2941. Maximum absorption observed at 502 nm, and maximum excitation observed at 516 nm (excited at 500 nm)

A detailed description of one or more embodiments is presented herein by way of exemplification and not limitation.

It has been discovered that an asymmetric fluorophore herein provides whole-cell fluorescent staining for use in determining a cell count, cell morphology, or cell phenotype. In an embodiment, the asymmetric fluorophore herein includes a BODIPY-based, whole-cell stain that is used directly in live cells or fixed cells. In some embodiments, the asymmetric fluorophore is an asymmetrical BODIPY-NHS ester made by a synthesis described herein and that advantageously and unexpectedly has an aqueous solubility with ability to cross a cellular membrane. Beneficially, the asymmetric fluorophore provide efficiently staining live and fixed cells, wherein the live cell and fixed cells are stained by the asymmetric fluorophore under similar staining conditions.

Without wishing to be bound by theory, it is believed that the asymmetric fluorophore is a BODIPY-NHS ester that is an activated fluorophore and reacts with primary amines on protein molecules disposed in the cytoplasm of the cell, the cellular membrane, or a surface of the cell. These reactions allow the asymmetric fluorophore to remain inside of the cell for long periods of time (until the protein is lost) thereby providing labeling of the cells under both living and fixed cellular conditions.

Whole-cell staining with the asymmetric fluorophore provides cell tracking, cell counting, cell morphology, or cell phenotyping and can be used in high content screening (HCS), quantitative fluorescence microscopy, and the like. The asymmetric fluorophore can be used with fixed cell samples as well as monitoring cell morphology and cell number during live cell experiments. He asymmetric fluorophore can stain cells to provide a persistent label in live or fixed cells for direct comparison between the two states (i.e., the live cells as compared with the fixed cells, both stained independently with the asymmetric fluorophore) that provides identification of an effect of labeling or fixation protocol on cellular presentation. This measurement information can be used to establish a mathematical model to predict cellular behavior during a dynamic change or population growth.

In an embodiment, the asymmetric fluorophore provides whole-cell fluorescent staining of cell surfaces, cytoplasmic proteins, compounds present in cells and provides contrast for an edge of the cell body. The asymmetric fluorophore stains cells in an absence of permeabilization of the cellular membrane or a presence of permeabilization of the cellular membrane. Moreover, the asymmetric fluorophore can be used to stain cells and to monitor dynamic changes of live cells over extended periods of time when stained with the asymmetric fluorophore. The asymmetric fluorophore do not have pH-sensitivity, complicated chromophore efficiency, photo bleaching, or cytotoxicity to cells at increased concentrations.

According to an embodiment, the asymmetric fluorophore comprises an asymmetrically derivatized 4,4-Difluoro-4-bora-3a,4a-diaza-s-indacene (trademarked as BODIPY®). In a certain embodiment, the asymmetric fluorophore is 4,4-difluoro-1,3-dimethyl-4-bora-3a,4a-diaza-s-indacene-2-propionic acid N-hydroxysuccinimide ester of formula 6

Formula 6

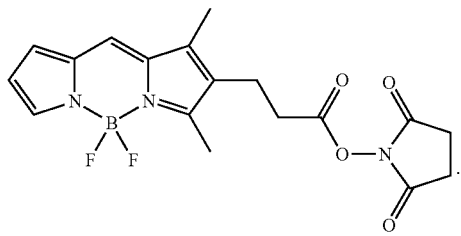

The asymmetric fluorophore provides high quantum yield, small stokes shift, high photostability, and relative insensitivity to cellular staining environment. Further, the asymmetric fluorophore includes a BODIPY core structure that is hydrophobic, which allows the asymmetric fluorophore to be cell permeable and includes a nonplanar hydrophilic moiety functionalized with a succinimidyl group that is compatible with the cytoplasm in terms of solubility.

In the asymmetric fluorophore, the core BODIPY structure offers several desirable physiochemical features for cell membrane permeability and cell labeling. The asymmetric fluorophore exhibits little charge, low polarity, and a partial planar structure facilitates communication through the lipid membrane of cells. By decreasing the planarity and symmetry from the core BODIPY structure in the asymmetric fluorophore, the asymmetric fluorophore has appreciable aqueous solubility. In the asymmetric fluorophore, functional groups were provided at the 7 and 6 (β-positions) and 5-position (α-position) of the BODIPY core to provide the asymmetric fluorophore with an asymmetrical molecular structure.

In an embodiment, a process for making the asymmetric fluorophore includes: decarboxylating a compound of formula 1

Formula 1

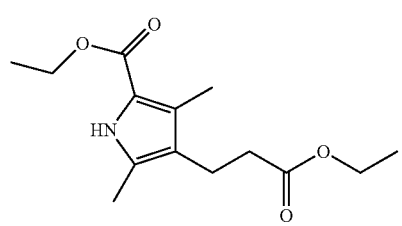

to form a compound of formula 2

Formula 2

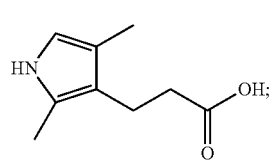

condensing the compound of formula 2 with 2-pyrrole aldehyde to form a compound of formula 3

Formula 3

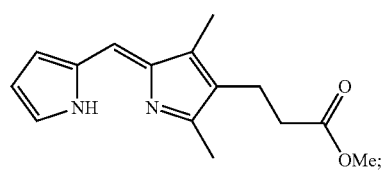

difluorinating the compound of formula 3 in a presence of boron trifluoride ethyl etherate to form a compound of formula 4

Formula 4

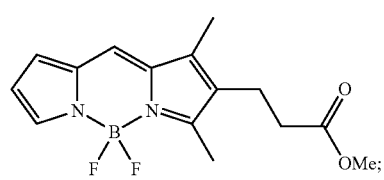

hydrolyzing the compound of formula 4 to form a compound of formula 5

Formula 5

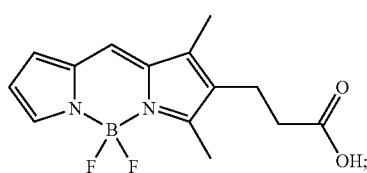

and succinimating the compound of formula 5 to form the asymmetric fluorophore comprising a compound of formula 6

Formula 6

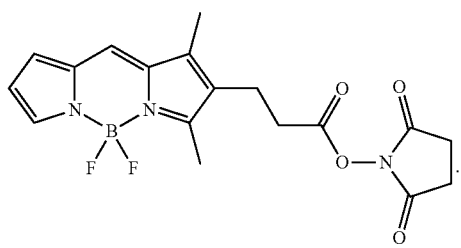

In the process decarboxylating the compound of formula 1 includes combining the compound of formula 1 with phosphoric acid. Performing the decarboxylation occurs at a temperature from 50° C. to 150° C., specifically from 60° C. to 120° C., and more specifically from 75° C. to 100° C.

In an embodiment, condensing the compound of formula 2 occurs in a presence of $POCl_3$, $POCl_3$, oxalyl chloride, thioyl chloride, any acid with pKa<5, and any Lewis acid. Difluorinating the compound of formula 3 can occurs in a presence of di-isopropylethylamine (DIPEA). Hydrolyzing the compound of formula 4 can occurs in a presence of a mineral acid (e.g., hydrochloric acid), an alkali metal hydroxide, a carbonate, an esterase to enzymatically hydrolyze the compound of formula 4.

According to an embodiment, succinimating the compound of formula 5 includes coupling the compound of formula 5 with N-hydroxysuccinimide. The compound of formula 5 also can be conjugated with a maleimide, isothiocyanate, tetrafluorophenyl ester, 4-sulfotetrafluorophenyl esters, sulfodicholorphenol ester, carbonyl azides, sulfonyl chloride, iodoacetamide, azide, alkyne, dichlorotriazine, N-methylisatoic anhydride, dansylaminophenylboronic acid, 9-anthroylnitrile, hydrazine, hydroxylamine, N-methyl-4-hydrazino-7-nitrobenzofurazan, biotin, aliphatic amine, aromatic amine, alkyl halide, N-hydroxysulfosuccinimide, or a combination thereof.

In an embodiment, a process for whole-cell staining includes decarboxylating the compound of formula 1 to form a compound of formula 2; converting the compound of formula 2 to form the asymmetric fluorophore including the compound of formula 6; combining the asymmetric fluorophore and a cell; and forming a radical of formula 7

Formula 7

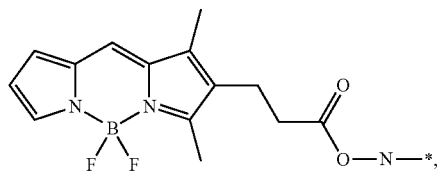

by reacting the asymmetric fluorophore with a primary amine in a cellular compound from the cell to irreversibly couple the radical of formula 7 to the cellular compound to stain the cell with the radical of formula 7 and to form a stained cellular compound having an amide linkage between the radical of formula 7 and the cellular compound, the cellular compound being a component of the cell prior to staining the cell with the radical of formula 7, wherein the stained cellular compound remains a part of the cell after staining the cell with the asymmetric fluorophore. In the radical of formula 7, wherein * is a point of attachment to a cellular compound Here, converting the compound of formula 2 to form the asymmetric fluorophore includes condensing the compound of formula 2 with 2-pyrrole aldehyde to form the compound of formula 3; difluorinating the compound of formula 3 in a presence of boron trifluoride ethyl etherate to form a compound of formula 4; hydrolyzing the compound of formula 4 to form a compound of formula 5; and succinimating the compound of formula 5 to form the asymmetric fluorophore. It is contemplated that decarboxylating the compound of formula 1 comprises combining the compound of formula 1 with phosphoric acid. Further, condensing the compound of formula 2 occurs in a presence of $POCl_3$, and difluorinating the compound of formula 3 occurs in a presence of di-isopropylethylamine, any triaklyamine, any base with pKa>7, or a combination thereof. Hydrolyzing the compound of formula 4 occurs in a presence of hydrochloric acid, and succinimating the compound of formula 5 comprises coupling the compound of formula 5 with N-hydroxysuccinimide.

In an embodiment, the cell comprises a live cell. In some embodiments, the cell comprises a fixed cell.

According to an embodiment, the asymmetric fluorophore is synthesized according to the following scheme:

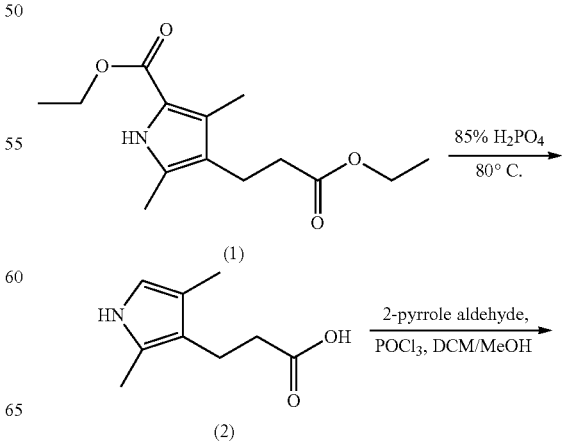

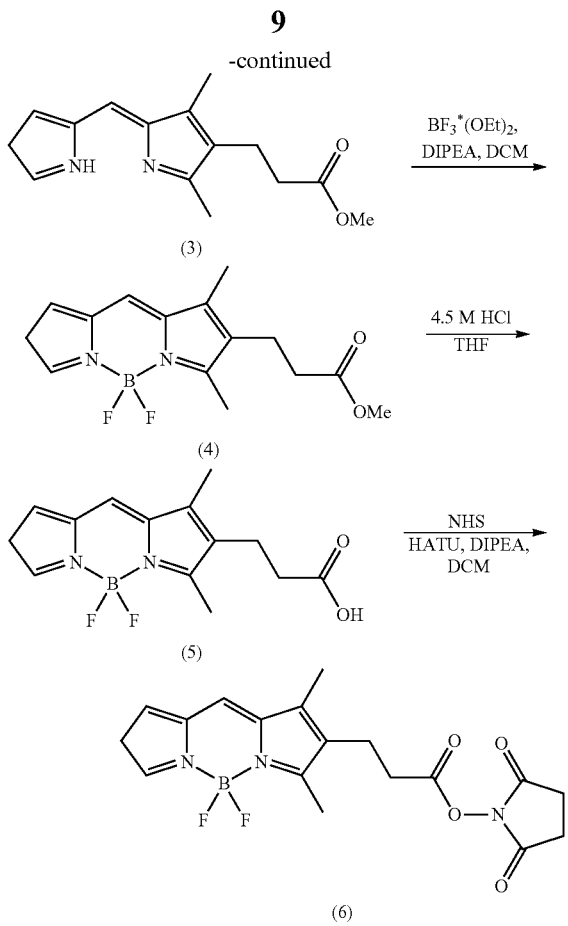

With regard to the compound of formula 2, treating the compound of formula 1 with hot 85% H₃PO₄ provided a yield of (2) to 80% and decreased an amount of side products. The condensation reaction between (2) and 2-pyrrole aldehyde was facilitated using one equivalent of POCl₃ in dichloromethane with 10% methanol. The addition of methanol allowed for the methyl ester to be formed and aided in purification. Methanol was removed from the reaction mixture, and the reaction mixture was dissolved in anhydrous dichloromethane. DIPEA and boron trifluoride ethyl etherate were subsequently added and the solution was stirred overnight. Purification, e.g., dry column vacuum chromatography, provided compound (3) with a yield of 87%. The methyl ester (4) was hydrolyzed with 4.5 M HCl to form (5) with a quantitative yield. The N-succinimidyl ester (6) was synthesized with 78% yield by coupling the free acid (5) to N-hydroxysuccinimide.

The resulting fluorophore (6) was soluble in aqueous solutions (pH independent) up to 1 μM and was diluted down to 0.1% DMSO from a 100 mM, 100% DMSO stock solution. Compound (6) had a maximum excitation at 502 nm and emission at 516 nm and a relative quantum yield of 0.84 in 10% aqueous methanol as shown in FIG. 1. Compound (6) has a sharp fluorescence peak and high quantum yield.

Figure 2:
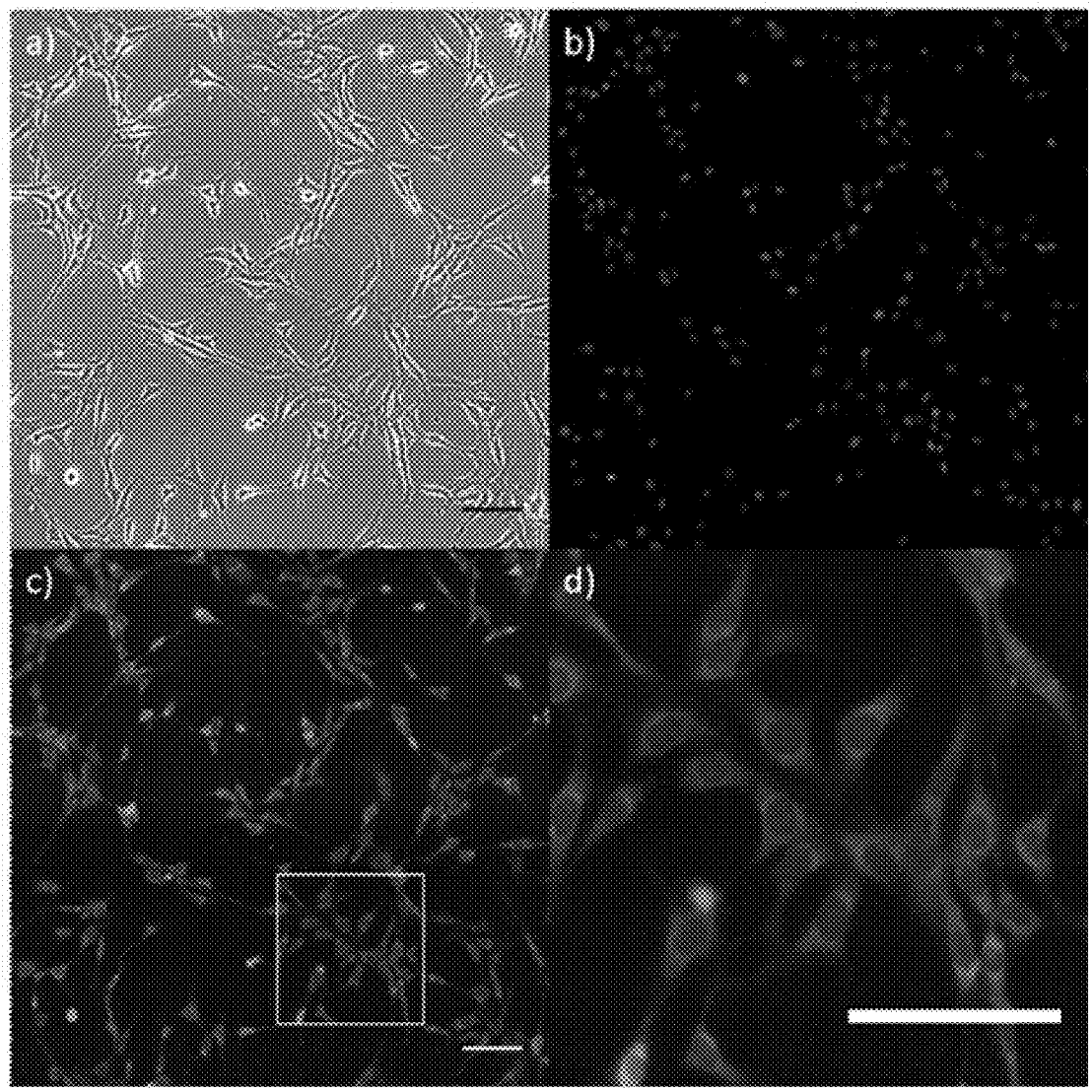
FIG. 2 shows microscopy of live NIH 3T3 cells after 30 minutes of staining with an asymmetric fluorophore. (a) Phase contrast, (b) Hoechst 33342 stain, (c) 1 µM asymmetric fluorophore, (d) close-up of image (c) outlined in yellow box. Fluorescent image taken at an exposure time of 1 second. Scale bars represent 100 µm.
Figure 3:
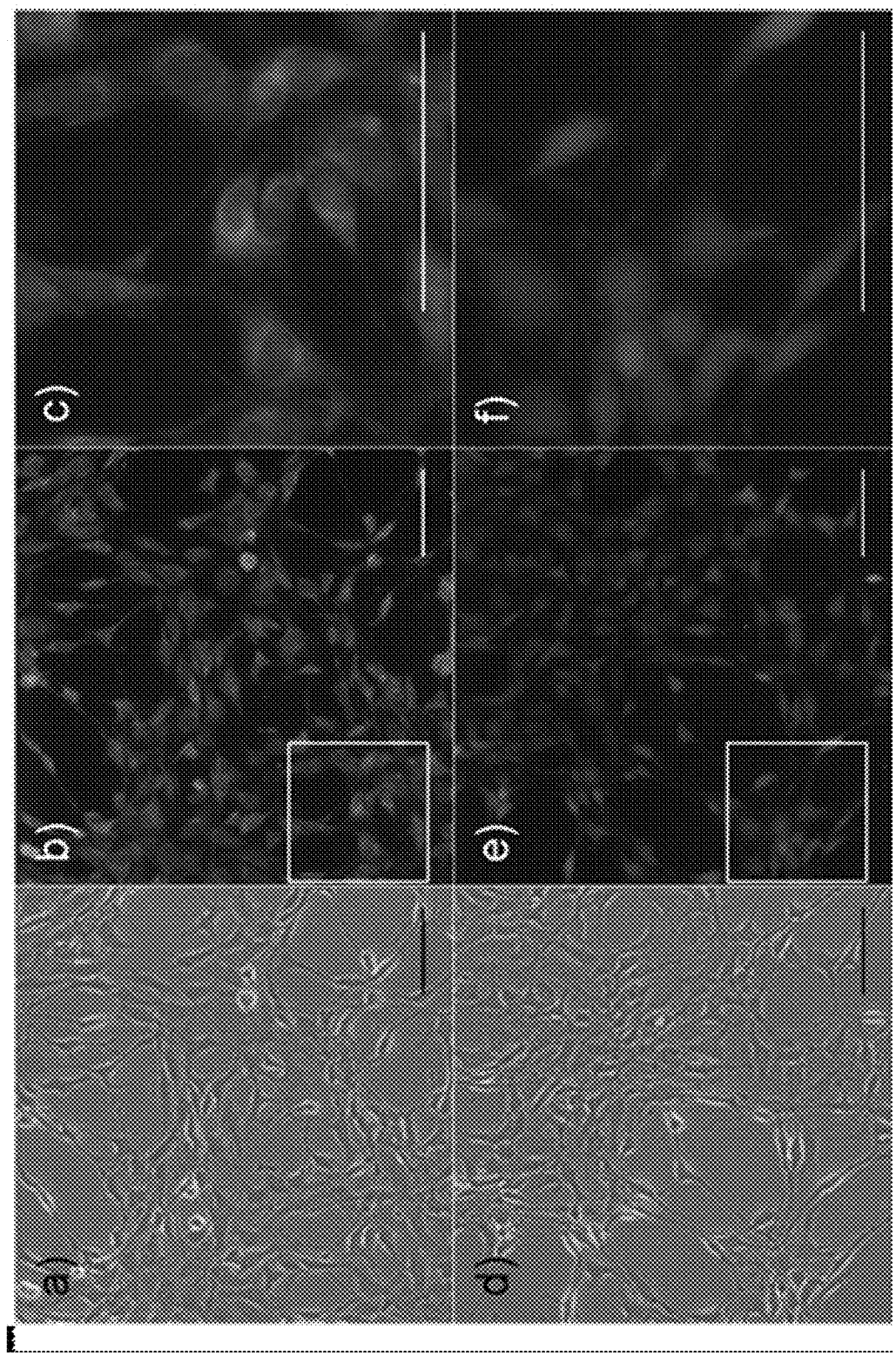
FIG. 3 shows microscopy of live NIH 3T3 cells stained with either asymmetric fluorophore or CFSE. NIH 3T3 cells stained with asymmetric fluorophore: (a) Phase contrast, (b) 100 nM asymmetric fluorophore, and (c) close-up of image (b) outlined in yellow box. NIH 3T3 cells stained with CFSE: (d) Phase contrast, (e) 100 nM CFSE, and (f) close-up of image (e) outlined in yellow box. Both fluorescence images are taken at same conditions at an exposure time of 1 second and no image enhancing processing was performed. Scale bars represent 100 µm.
Figure 4:
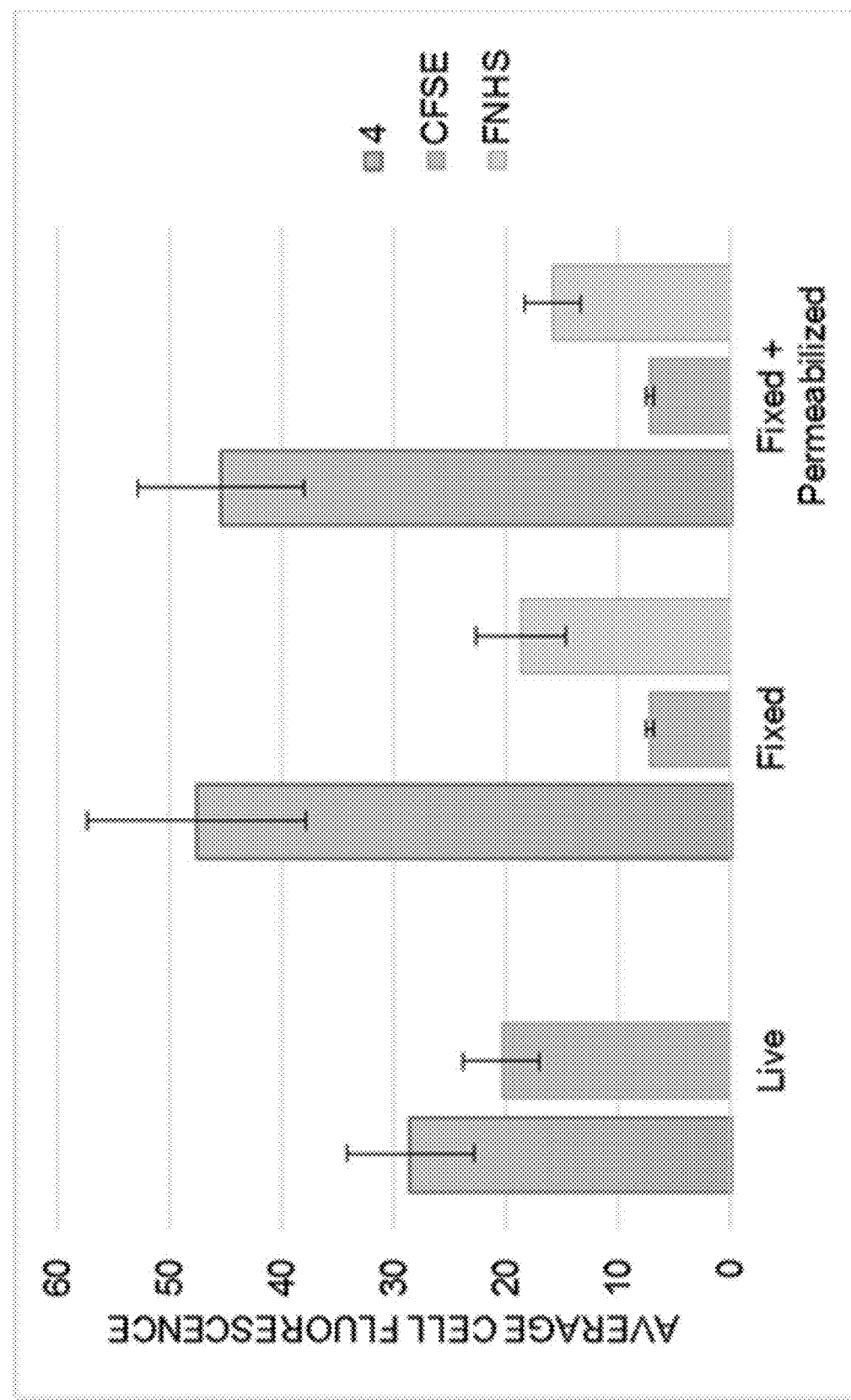
FIG. 4 shows average fluorescence intensities of individual NIH 3T3 cells stained with asymmetric fluorophore, CFSE, and FNHS (all at 1 µM) which are live, fixed, or fixed and permeabilized. All images taken under same conditions at an exposure time of 1 second. Error bars represent average standard deviation from three different experiments.

The asymmetric fluorophore (6) functions as a whole cell stain in both live and fixed cells. Further, the asymmetric fluorophore stains live cells brightly, has low background staining, and is non-toxic when used at concentrations that provide suitable signal for image analysis segmentation routines on fluorescence images of live cells. Also, the asymmetric fluorophore stains fixed cells. FIG. 2 shows that with live NIH 3T3 cells, the asymmetric fluorophore crossed the cell membrane and stained the cytoplasmic regions with some nuclear staining. FIG. 2 also shows that the asymmetric fluorophore efficiently and permanently labels live cells that can subsequently be tracked or imaged after a number of days. The staining pattern of the asymmetric fluorophore in cells was compared to carboxyfluorescein succinimidyl ester (CFSE) as a standard NHS ester fluorophore used in cell labeling. FIG. 3 shows staining of NIH 3T3 cells with the asymmetric fluorophore and CFSE under the same conditions and concentrations. Visually, CFSE appears to have a more diffuse staining pattern than the asymmetric fluorophore. The asymmetric fluorophore selectively stains intercellular amines, resulting in a less diffuse staining. Quantitative, total differences between the live cell fluorescence intensities of the CFSE and the asymmetric fluorophore are shown in FIG. 4.

Figure 5:
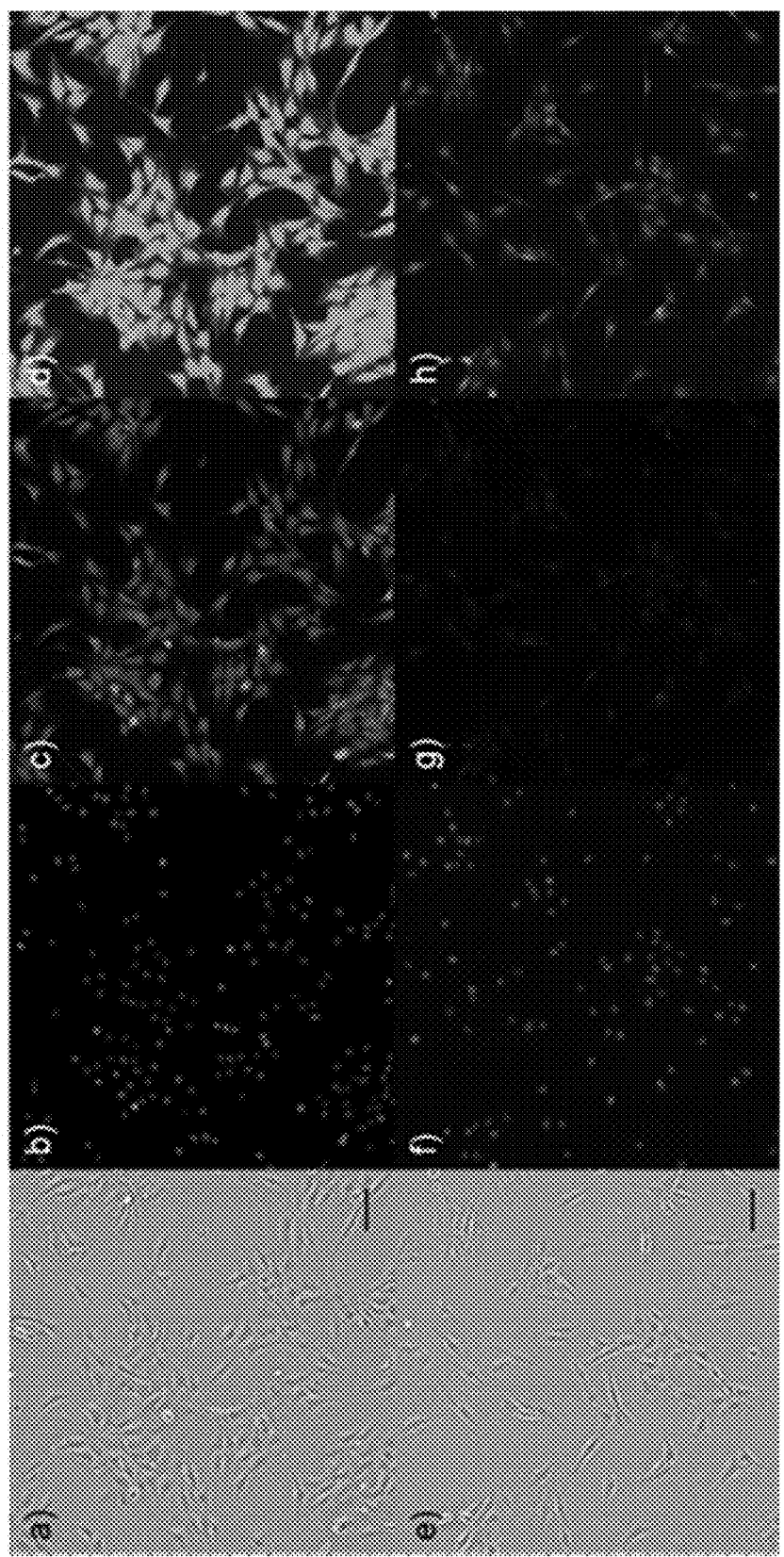
FIG. 5 shows microscopy of 5% paraformaldehyde fixed NIH 3T3 cells stained with either asymmetric fluorophore or FNHS. NIH 3T3 cells stained with asymmetric fluorophore: (a) Phase contrast, (b) Hoechst 33342 stain, (c) 1 µM asymmetric fluorophore, and (d) maximum displayed value in decreased by 4-fold. NIH 3T3 cells stained with FNHS: (e) Phase contrast, (f) Hoechst 33342 stain, (g) 1 µM FNHS, and (h) maximum displayed value in decreased by 4-fold. Both fluorescence images taken at same conditions at an exposure time of 200 ms.

Fixed and permeabilized cells were tested with the asymmetric fluorophore, and the non-diacetate conjugate of CFSE, 5(6)-carboxy fluorescein-N-hydroxysuccinimidyl ester (FNHS), as standard NHS ester fluorophores. CFSE is dependent on enzymatic activity to cleave the di-ester to become fluorescent and may be unreliable to use in fixed cells. FIG. 5 shows stains of NIH 3T3 cells with the asymmetric fluorophore and FNHS under the same conditions and concentrations. The asymmetric fluorophore appeared brighter than FNHS. Quantitative analysis of these images, as shown in FIG. 4, shows that under the fixed conditions, the asymmetric fluorophore was three fold brighter than FNHS.

Figure 6:
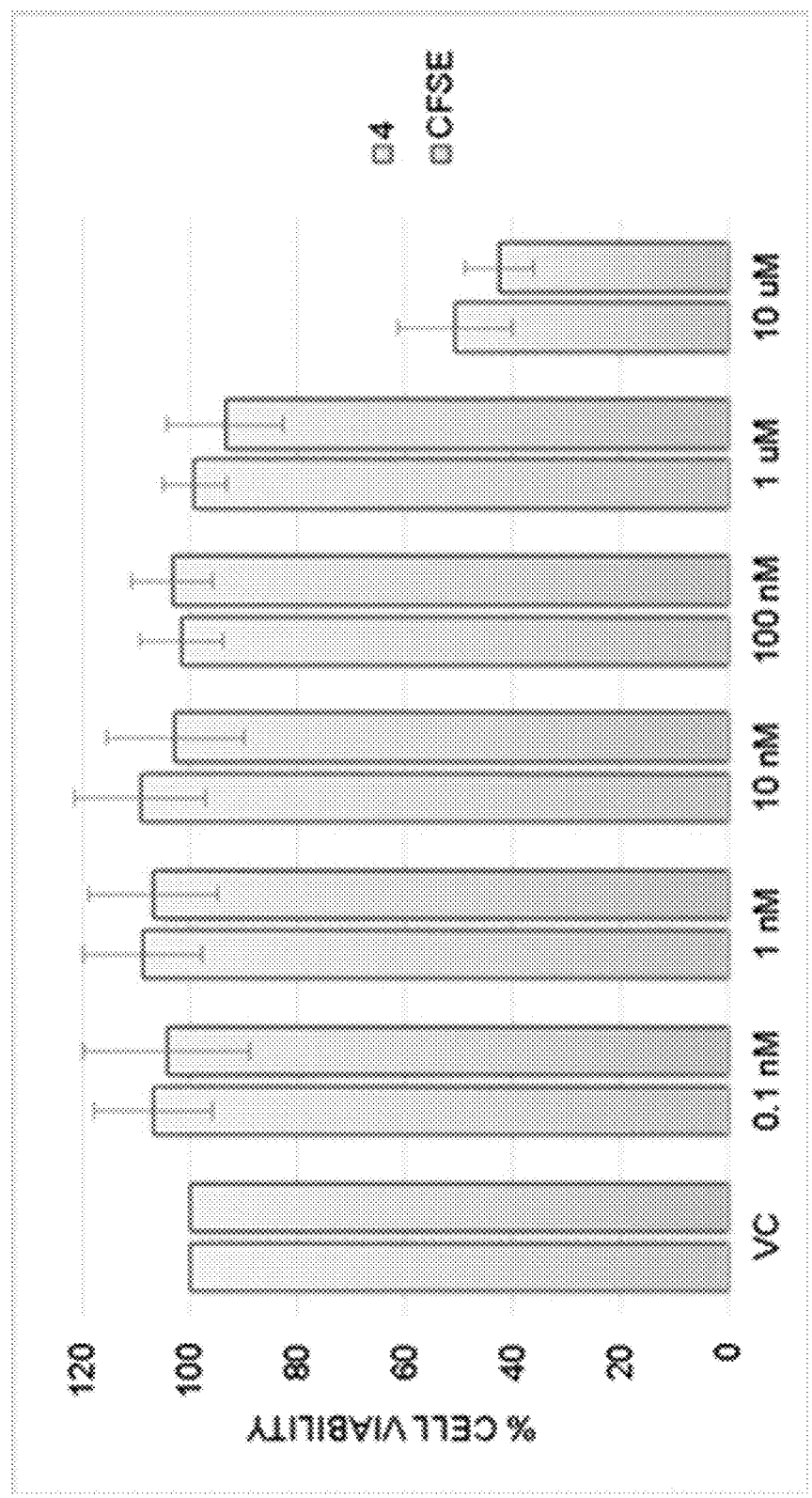
FIG. 6 shows basal cytotoxicity MTS assay of asymmetric fluorophore and CFSE in NIH 3T3 cells after 72 hours of initial treatment. VC: vehicle control (0.1% DMSO), error bars represent standard deviation, n=9.

A 3-(4,5-dimethylthiazol-2-yl)-5-(3-carboxymethoxyphenyl)-2-(4-sulfophenyl)-2H-tetrazolium (MTS) assay was used to assess toxicity of the asymmetric fluorophore in NIH 3T3 cells. FIG. 6 shows there was no significant change in cell viability for concentrations of the asymmetric fluorophore below 10 μM during a 72-hour incubation.

The ease of synthesis, capability to stain both live and fixed cells, and low toxicity of the asymmetric fluorophore make it a highly useful fluorophore that provides a stain for fluorescent study of cells.

The articles and processes herein are illustrated further by the following Examples, which are non-limiting.

EXAMPLES

Example 1

Synthesis of 4,4-difluoro-1,3-dimethyl-4-bora-3a, 4a-diaza-s-indacene-2-propionic acid methyl ester (4)

Figure 7:
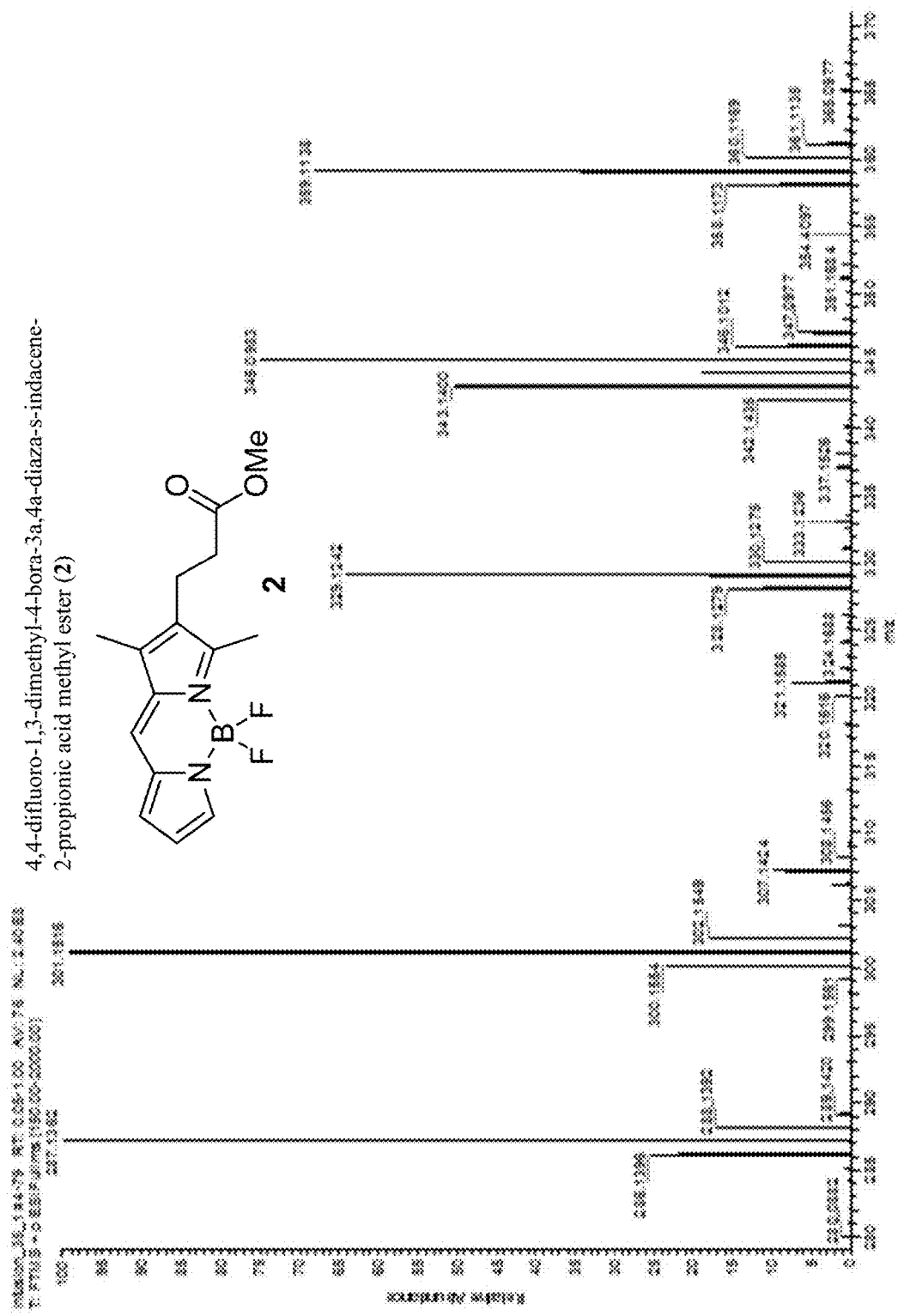
FIG. 7 shows a graph of relative abundance versus m/z for 4,4-difluoro-1,3-dimethyl-4-bora-3a, 4a-diaza-s-indacene-2-propionic acid methyl ester (2)
Figure 8:
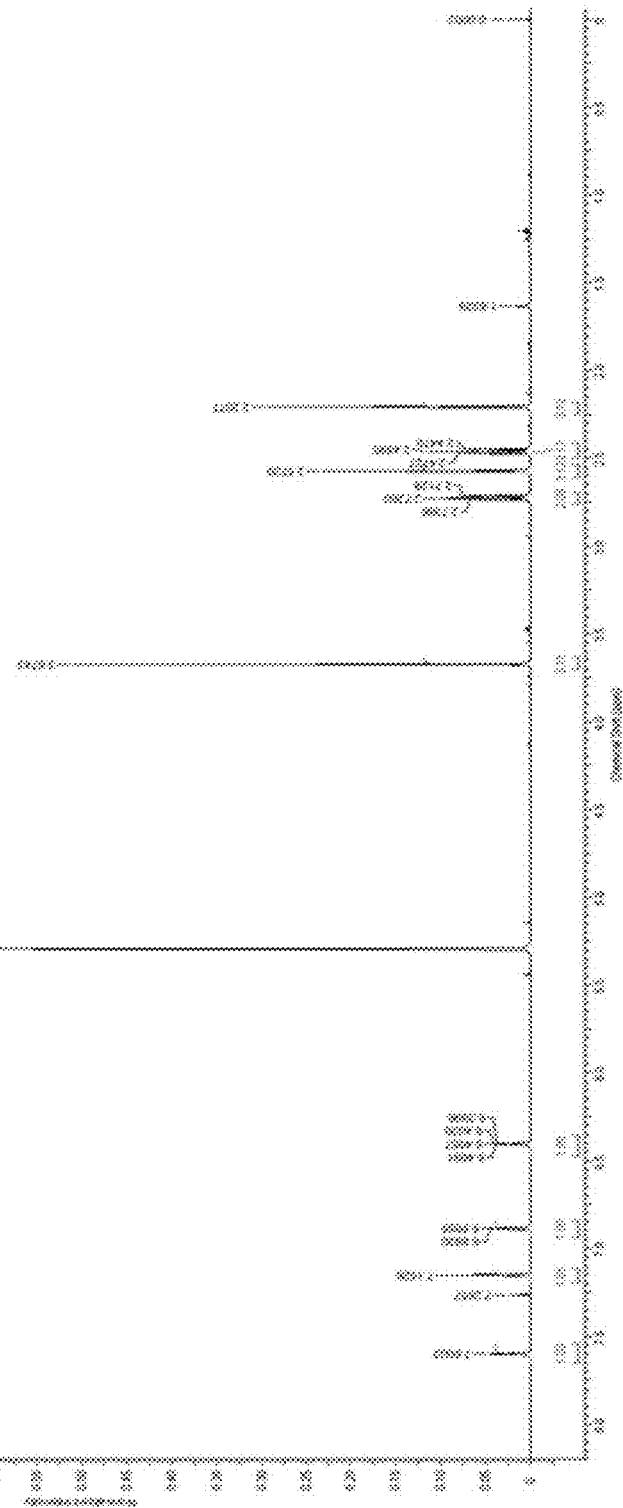
FIG. 8 shows a graph of normalized intensity versus chemical shift for 4,4-difluoro-1,3-dimethyl-4-bora-3a,4a-diaza-s-indacene-2-propionic acid methyl ester (2)
Figure 9:
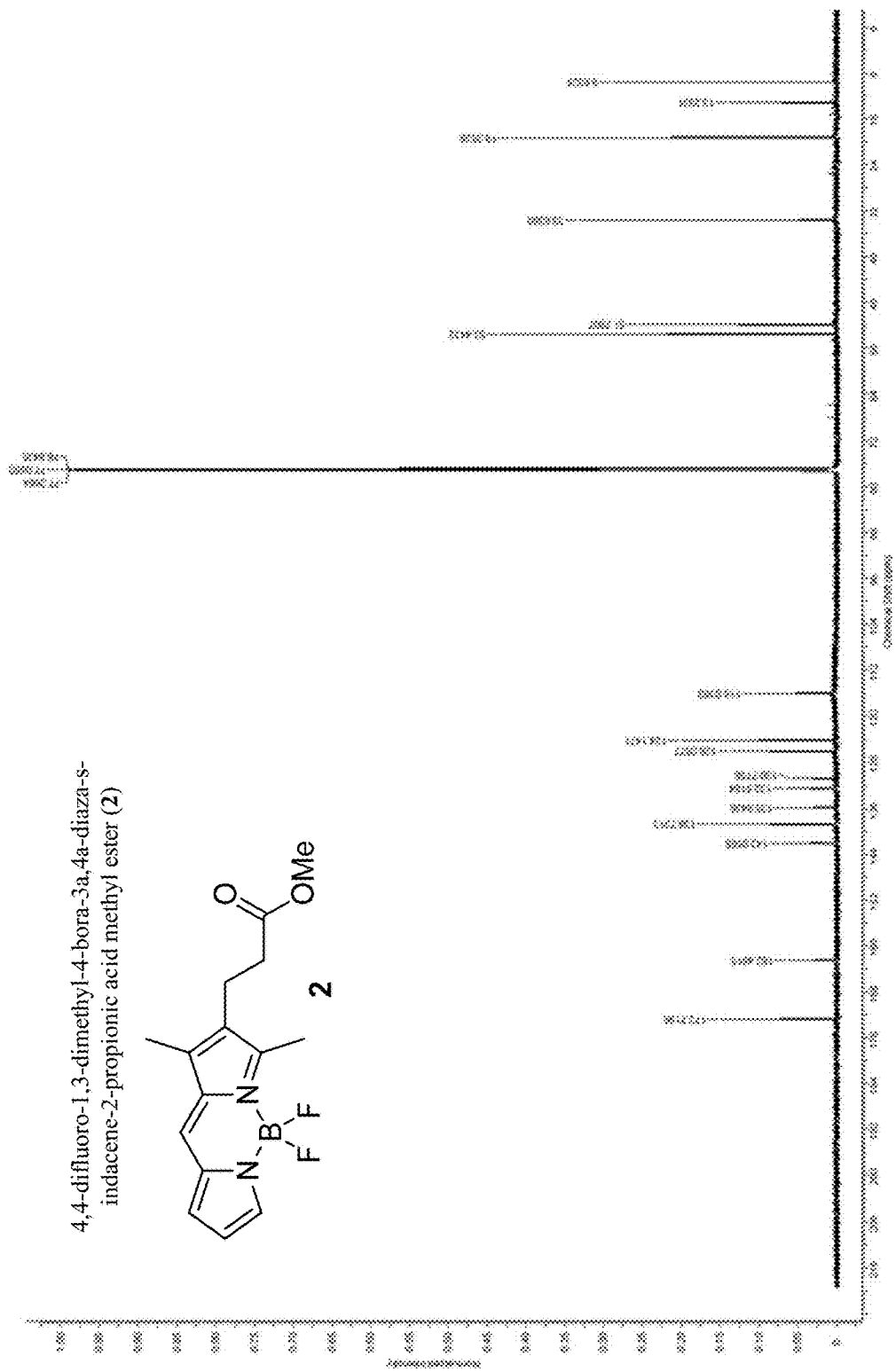
FIG. 9 shows a graph of normalized intensity versus chemical shift for 4,4-difluoro-1,3-dimethyl-4-bora-3a,4a-diaza-s-indacene-2-propionic acid methyl ester (2)

3-(2,4-Dimethyl-1H-pyrrol-3-yl)propanoic acid (2) (1.45 g, 0.00867 mol) and 2-pyrrole aldehyde (0.91 g, 1.1 eq, 0.00954 mol) were dissolved in 10 mL 10:1 (v:v) anhydrous dichloromethane:methanol and stirred at 0° C. under nitrogen protection. POCl₃ (1.46 g, 1.1 eq, 0.00954 mol) was added drop-wise (15 min) to the mixture and the resulting solution was stirred and allowed to heat to room temperature over 6 hrs. The reaction mixture was then evaporated under reduced pressure (~0.5 mL) and then re-dissolved with 10 mL of anhydrous dichloromethane. The reaction mixture was stirred at 0° C. under nitrogen protection and then, sequentially, boron trifluoride ethyl etherate (4.31 g, 4 eq, 0.0347 mol) and di-isopropylethylamine (4.92 g, 4 eq, 0.0347 mol) were added drop-wise over 30 min. The reaction was left to stir overnight (13 hr) at room temperature under nitrogen protection. The reaction mixture was added to deionized H₂O (100 mL) and then extracted three times with dichloromethane (150 mL total). The combined organic layers were then washed with brine, dried over $Na_2SO_4$, filtered, and evaporated to dryness under reduced pressure. The resultant metallic green oil was dissolved in 10 mL dichloromethane and then absorbed onto 10 g celite and evaporated to dryness under reduced pressure. The crude reaction mixture was then purified using dry column vacuum chromatography (silica gel, 100:1 (v:v) dichloromethane: methanol) affording 2.65 g (87%) of compound (4). High resolution mass spectrometry (HRMS) as shown in FIG. 7: $C_{15}H_{17}BF_2N_2O_2$ [M+Na]⁺ Calculated: 329.1249. Found: 329.1242. ¹H NMR as shown in FIG. 8 (600 MHz, CDCl₃, 24.97° C., TMS) δ (ppm) 7.60 (s, 1H), 7.15 (s, 1H), 6.89 (s, 1H), 6.41 (s, 1H), 3.67 (s, 1H), 2.73 (t, j=7.89 Hz, 2H), 2.57 (s, 3H), 2.46 (t, j=7.52 Hz, 2H), 2.21 (s, 3H). ¹³C NMR as shown in FIG. 9 (150 MHz, CDCl₃) δ (ppm) 172.72, 162.48, 142.06, 138.73, 135.84, 132.52, 130.78, 126.06, 124.15, 116.04, 51.78, 33.64, 19.35, 13.29, 9.63.

Example 2

Synthesis of 4,4-difluoro-1,3-dimethyl-4-bora-3a, 4a-diaza-s-indacene-2-propionic acid (5)

Figure 10:
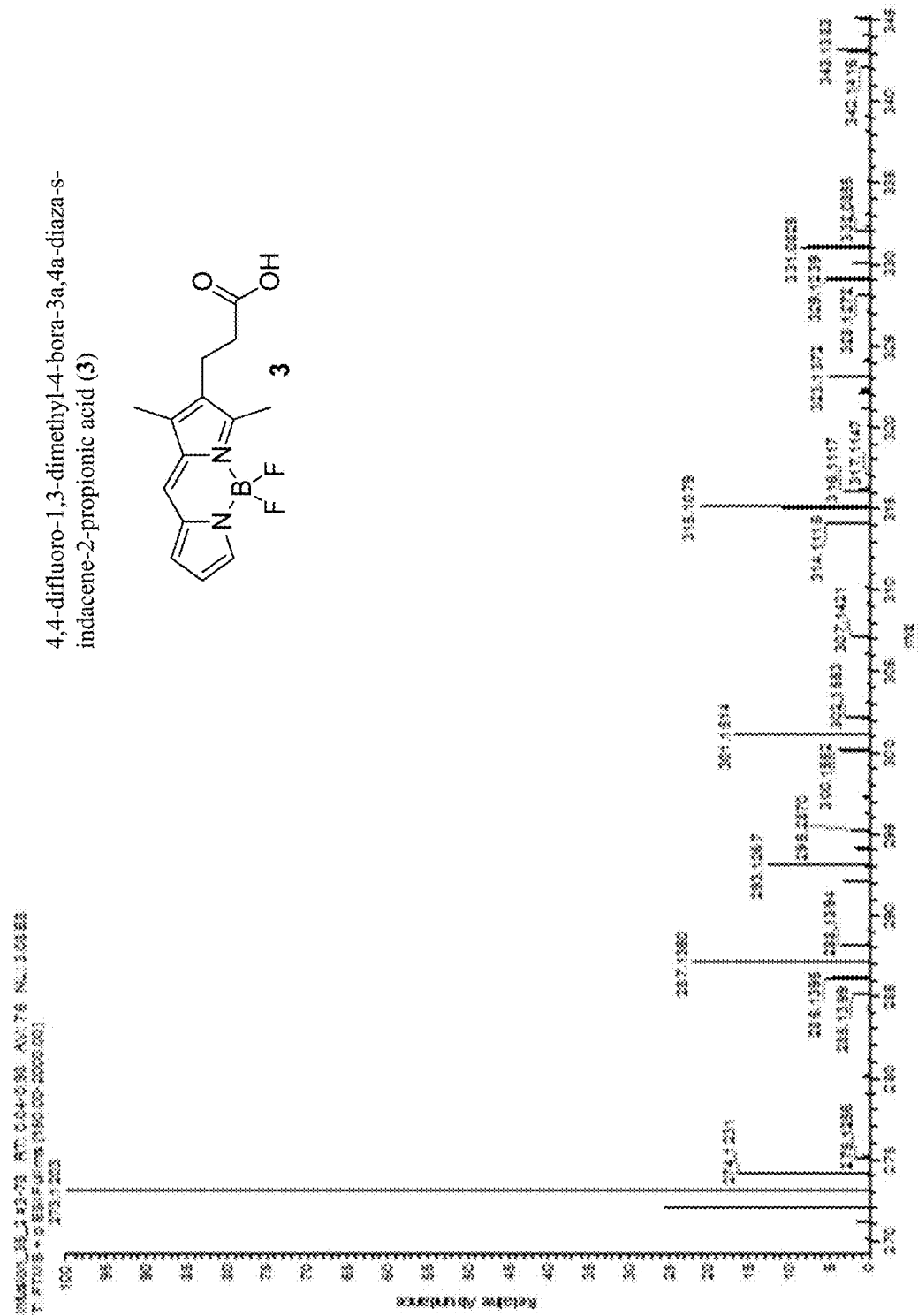
FIG. 10 shows a graph of relative abundance versus m/z for 4,4-difluoro-1,3-dimethyl-4-bora-3a,4a-diaza-s-indacene-2-propionic acid (3)
Figure 11:
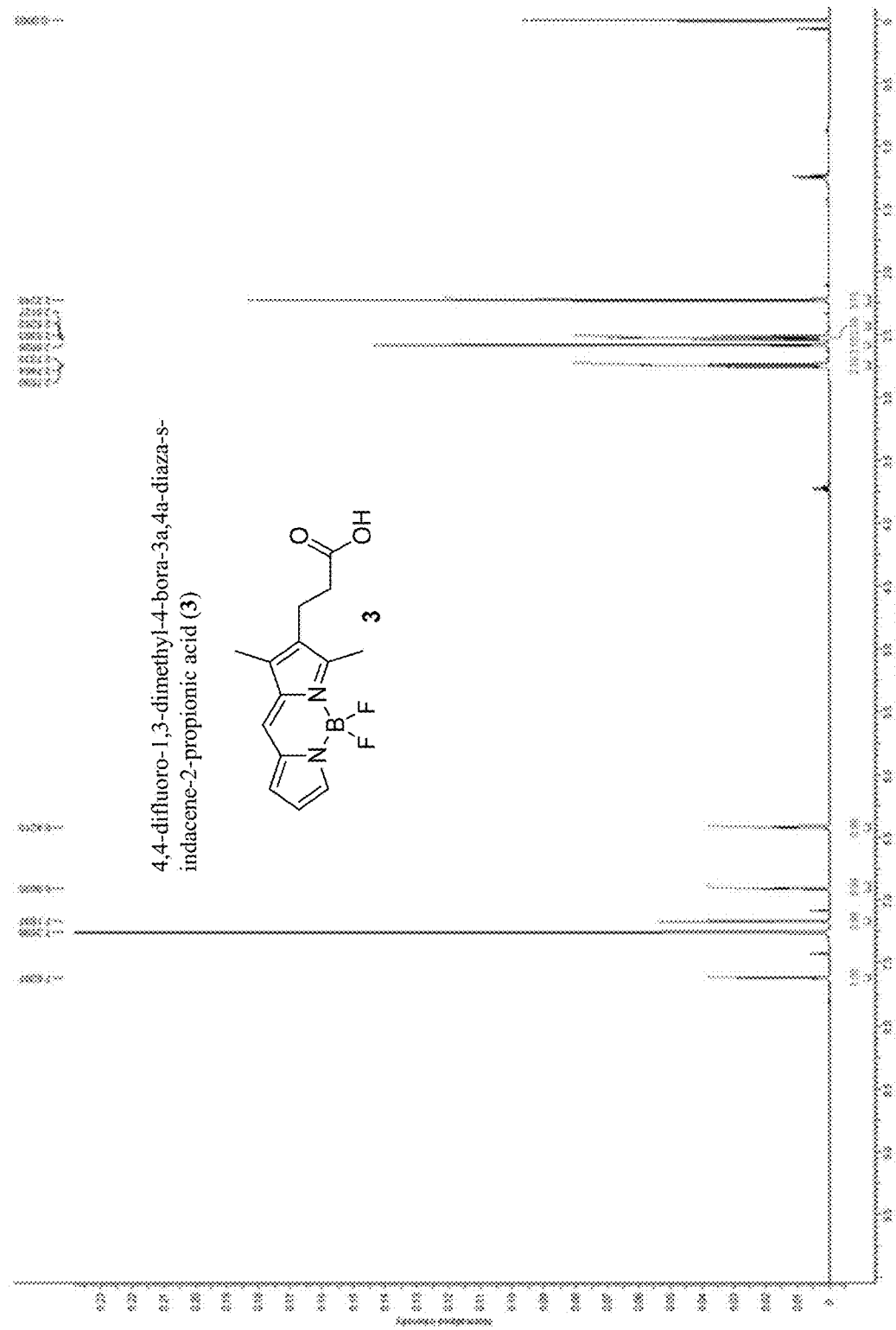
FIG. 11 shows a graph of normalized intensity versus chemical shift for 4,4-difluoro-1,3-dimethyl-4-bora-3a,4a-diaza-s-indacene-2-propionic acid (3)
Figure 12:
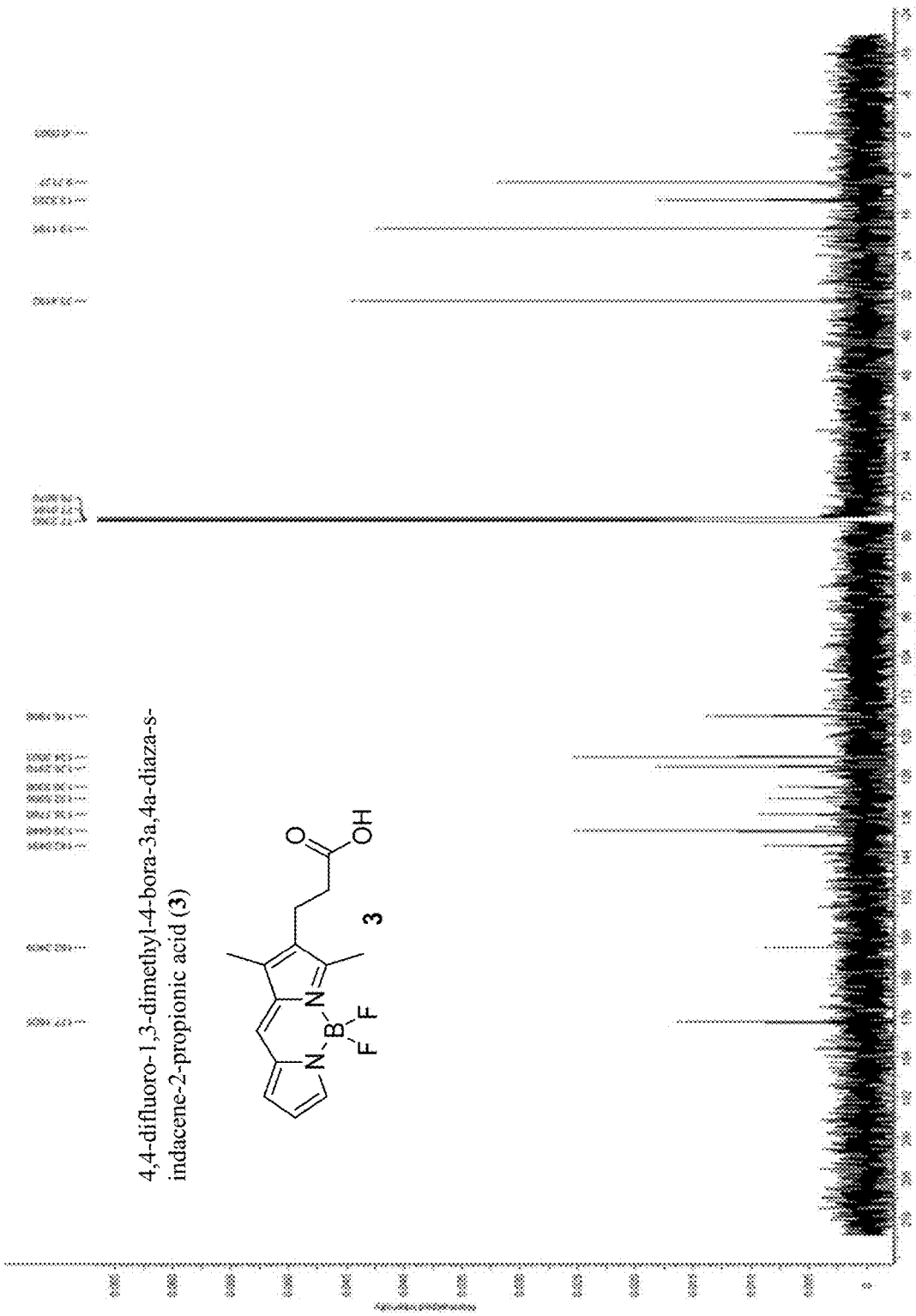
FIG. 12 shows a graph of normalized intensity versus chemical shift for 4,4-difluoro-1,3-dimethyl-4-bora-3a,4a-diaza-s-indacene-2-propionic acid (3)

4,4-Difluoro-1,3-dimethyl-4-bora-3a,4a-diaza-s-indacene-2-propionic acid methyl ester (4) (1.46 g, 0.00477 mol) was dissolved in tetrahydrofuran (9.8 mL) and dH₂O (3.3 mL) and stirred at 0° C. Concentrated HCl (4 mL) was then added drop-wise and the reaction was allowed to stir until completed (1 hr, TLC). Upon completion the reaction mixture was extracted with 10 mL dichloromethane three times. The combined organic layers were washed with brine, dried over $Na_2SO_4$, filtered, and evaporated to dryness under reduced pressure. A total of 1.4 g (quant.) of compound 3 was received and used without further purification. HRMS as shown in FIG. 10: $C_{14}H_{15}BF_2N_2O_2$ [M+Na]⁺ Calculated: 315.1092. Found: 315.1079. ¹H NMR as shown in FIG. 11 (600 MHz, CDCl₃, 24.97° C., TMS) δ (ppm) 7.60 (s, 1H), 7.17 (s, 1H), 6.90 (s, 1H), 6.42 (s, 1H), 2.75 (t, j=7.89 Hz, 2H), 2.58 (s, 3H), 2.53 (t, j=7.52 Hz, 2H), 2.22 (s, 3H). ¹³C NMR as shown in FIG. 12 (150 MHz, CDCl₃) δ (ppm) 177.16, 162.24, 142.05, 139.04, 135.78, 132.60, 130.33, 126.29, 124.30, 116.20, 33.42, 19.12, 13.32, 9.71.

Example 3

Synthesis of 4,4-difluoro-1,3-dimethyl-4-bora-3a, 4a-diaza-s-indacene-2-propionic acid N-hydroxysuccinimide ester (6)

Figure 13:
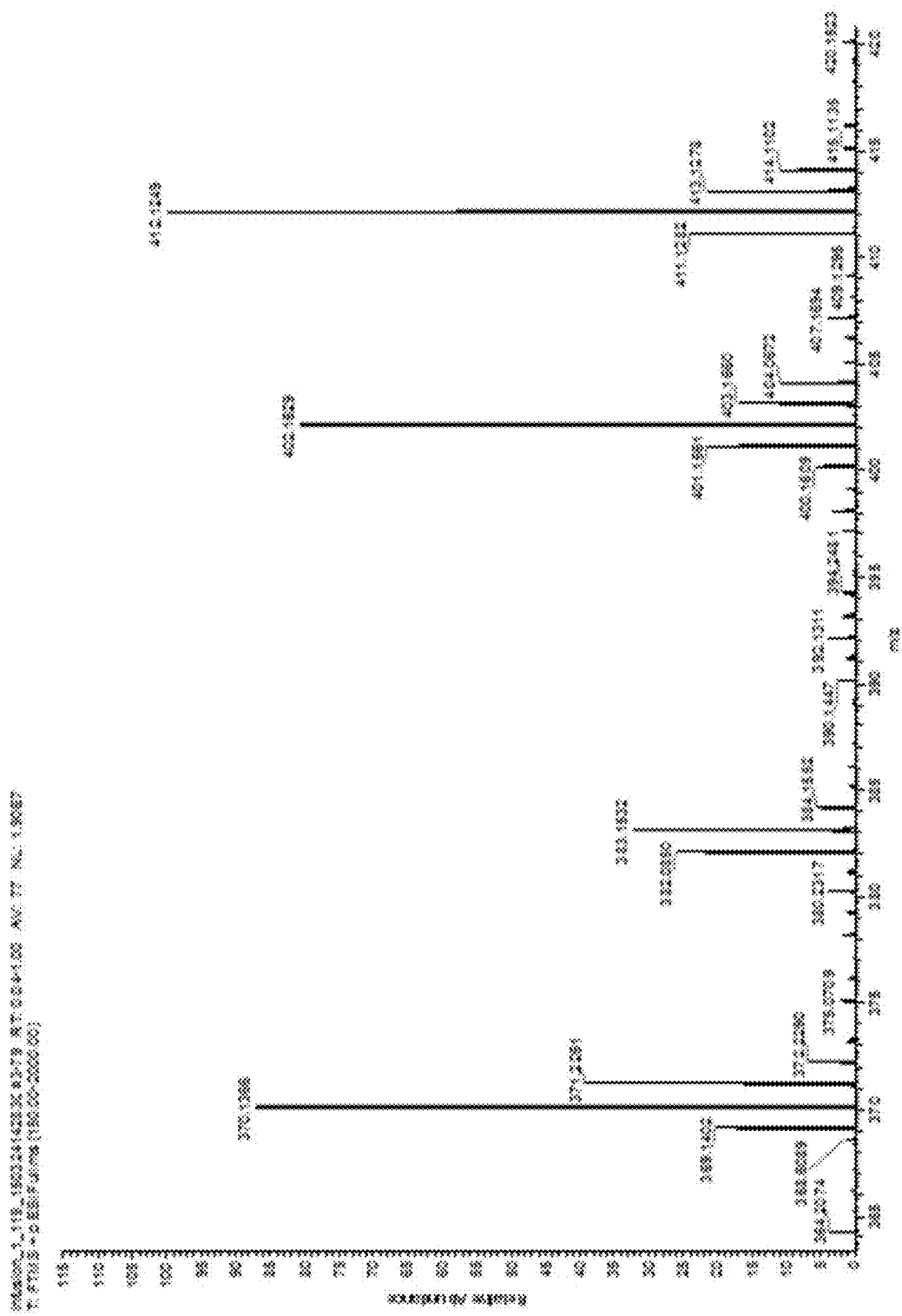
FIG. 13 shows a graph of relative abundance versus m/z for an asymmetric fluorophore.
Figure 14:
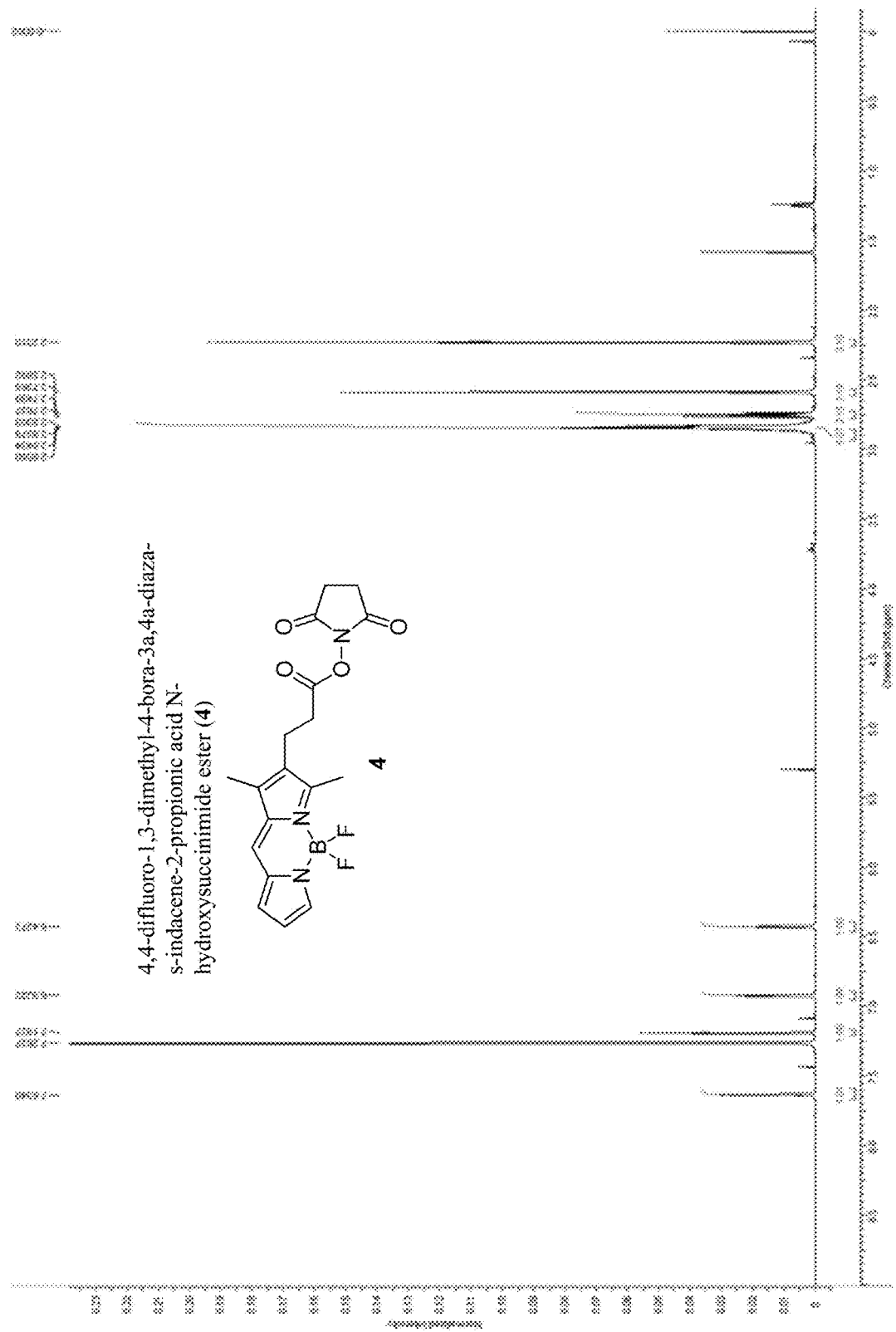
FIG. 14 shows a graph of normalized intensity versus chemical shift for an asymmetric fluorophore.
Figure 15:
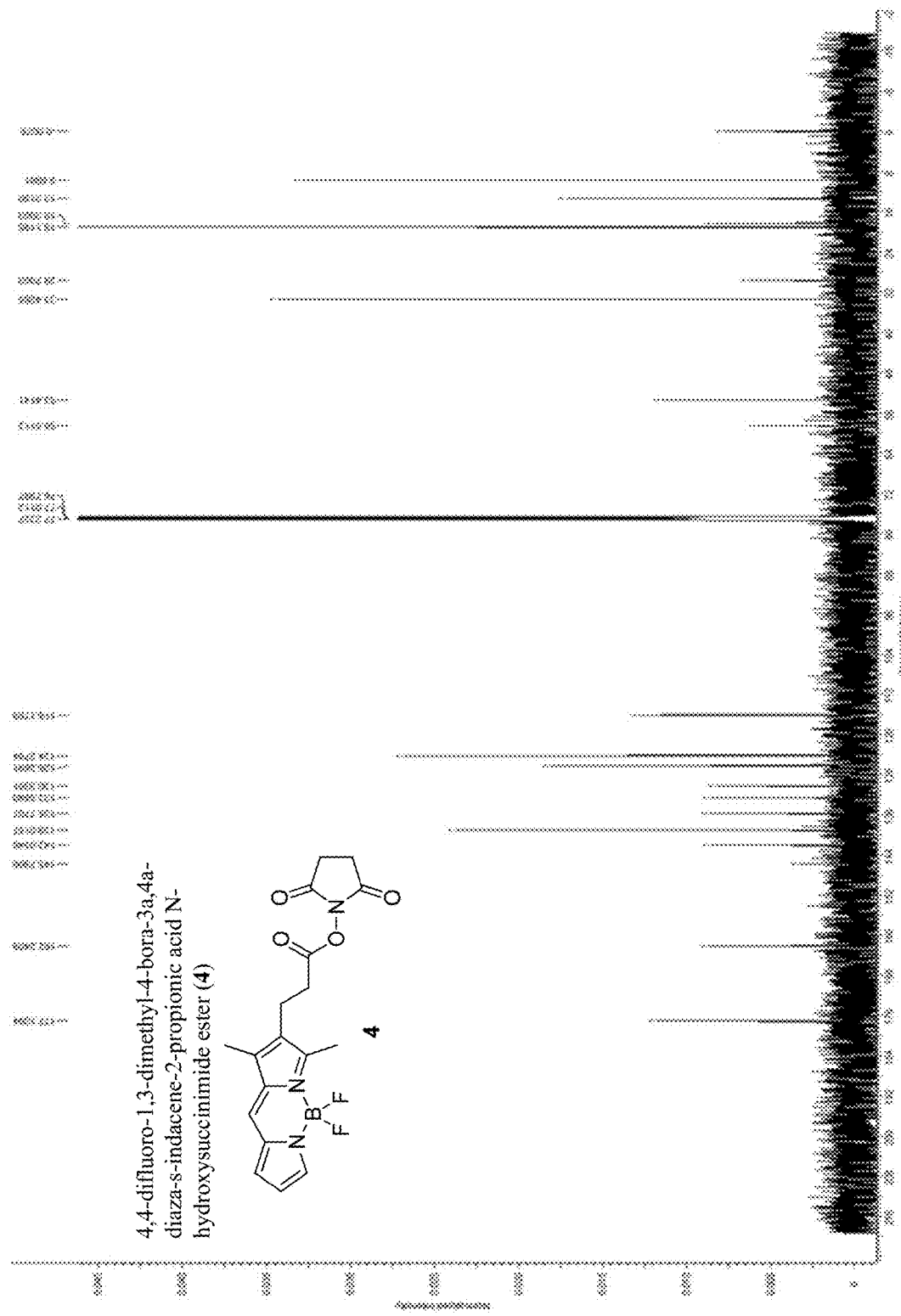
FIG. 15 shows a graph of normalized intensity versus chemical shift for an asymmetric fluorophore.
Figure 16:
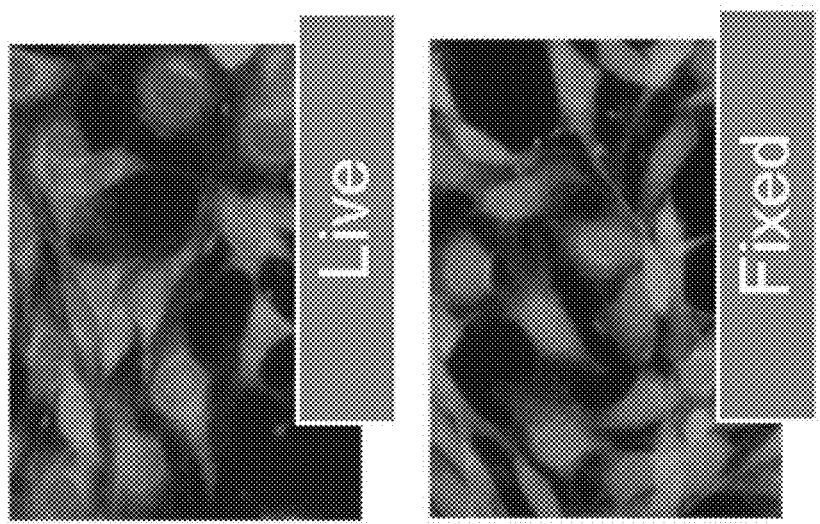
FIG. 16 shows a live sample and fixed sample stained with an asymmetric fluorophore.
Figure 16:
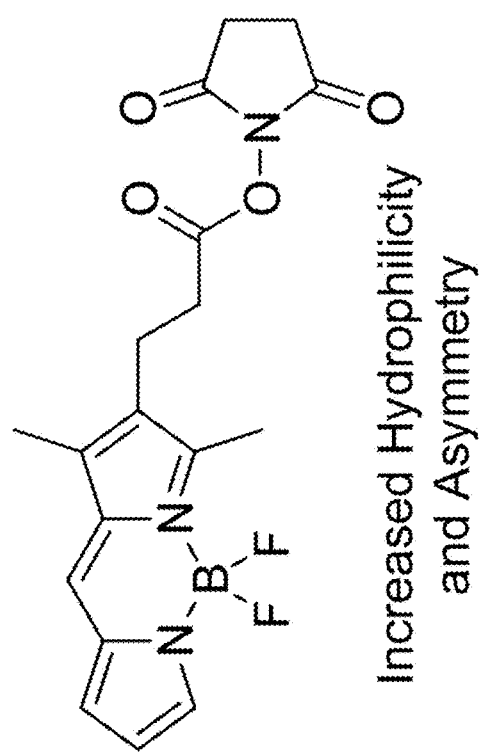

4,4-Difluoro-1,3-dimethyl-4-bora-3a,4a-diaza-s-indacene-2-propionic acid (5) (0.06 g, 0.000205 mol) was dissolved in anhydrous dichloromethane (10 mL) and to it HATU (0.12 g, 1.5 eq, 0.000308 mol) and DIPEA (0.11 mL, 3 eq, 0.000616 mol) were added and stirred under nitrogen protection for 10 mins. N-Hydroxysuccinimide (0.071 g, 3 eq, 0.000616 mol) dissolved in 5 mL anhydrous dichloromethane was then added drop-wise and the reaction was stirred for 1 hr. Upon completion, the reaction mixture was added to water (20 mL), extracted with dichloromethane (30 mL), washed with brine, dried over $Na_2SO_4$, filtered, and evaporated to dryness under reduced pressure. The crude product was purified using column chromatography (silica gel, 10:1 (v:v) dichloromethane:methanol). A total of 0.062 g (78%) of compound 6 was received. HRMS as shown in FIG. 13: $C_{18}H_{18}BF_2N_3O_4$ [M+Na]⁺ Calculated: 412.1256. Found: 412.1249. ¹H NMR as shown in FIG. 14 (600 MHz, CDCl₃, 24.97° C., TMS) δ (ppm) 7.63 (s, 1H), 7.19 (s, 1H), 6.92 (s, 1H), 6.42 (s, 1H), 2.85-2.83 (m, 6H), 2.75 (t, j=8.07 Hz, 2H), 2.59 (s, 3H), 2.23 (s, 3H). ¹³C NMR as shown in FIG. 15 (150 MHz, CDCl₃) δ (ppm) 168.92, 167.51, 161.70, 142.16, 139.40, 135.63, 132.70, 129.16, 126.60, 124.68, 116.35, 30.75, 25.58, 19.09, 13.32, 9.76.

Example 4

Photophysical Characterization

The UV-Vis and fluorescence emission spectra were recorded on a Synergy HT (BioTek Instruments, Inc.) multi-detection microplate reader equipped with a 10 W Xe flash light source for absorbance and a 20 W tungsten quartz halogen source for fluorescence. Relative quantum yields were determined using rhodamine 6G in ddH₂O as a reference while keeping instrument temperature and parameters constant. Serial dilutions of the asymmetric fluorophore (6) were made from a methanol stock; therefore, all dilutions of asymmetric fluorophore (6) were kept at 10% MeOH in water. All fluorescent spectra were intensity corrected using NIST SRM 2941 (excitation wavelength at 427 nm, scan emission monochromator from 450 nm to 650 nm using a 1 nm increment).

Example 5

Cell Culture and Imaging

NIH 3T3 cell line was obtained from ATCC (Manassas, Va.) and cultured routinely using sterile technique. Cell culture media consisted of DMEM supplemented with 10% FBS and 4 mM GlutaMax (Life Technologies). Both live and fixed cell automated microscopy was performed on a Zeiss AxioObserver Z1 (Carl Zeiss MicroImaging Inc., Jena, Germany) with an EC Plan-Neofluar 10×/0.30 Ph 1 objective (Carl Zeiss, Jena, Germany), and a Coolsnap HQ2 camera (Photometrics, Tucson, Ariz.). All fluorescent microscopy images were collected using a HE38 filter set (Carl Zeiss, Jena, Germany), a Colibri.2 LED light source at 100% intensity, and an exposure time of either 200 ms or 1 second. Performance benchmarking of the fluorescence microscope was performed daily. All imaging was done on the same day on the same microscope to decrease variations in image intensities. ImageJ (National Institutes of Health, Bethesda, Md.) was used to create figures and to determine the mean fluorescence intensity of cells.

Example 6

Live Cell Imaging

One day prior to imaging, NIH 3T3 cells were seeded at 10,000 cells per well in a 24-well plate (Corning Costar, TC-treated). After 24 hours of incubation (37° C., 5% CO₂), the media was removed from the plate and cells were washed once with DPBS (Ca and Mg free, Life Sciences). A total of 320 μL of DPBS with glucose was added to each well, and then 40 μL of Hoechst 33342 (final concentration of 0.5 μg/mL) and 40 μL of 4 (final concentrations from 10 μM to 1 nM were tested, final DMSO concentration=0.1%) or CFSE (final concentrations from 10 μM to 1 nM were tested, final DMSO concentration=0.1%). Cells were incubated (37° C., 5% CO₂) for 30 minutes, then rinsed one time with DPBS (Ca and Mg free, Life Sciences) and 500 μL of CO$_2$ independent media (Life Sciences, phenol red free, supplemented with 4 mM GlutaMax [Life Technologies]) was added to each well. Cells were then imaged at 37° C. using a total of 20 tiles per well with a 20% overlap. Each tile included 3 channel acquisitions: phase contrast, Hoechst 33342, 4/CFSE/FNHS (Zeiss F38 filter, 470 nm LED @100% power, at either 200-ms or 1000-ms exposure). Images were stitched using the Hoechst channel as the reference channel with Zen 2012 (V1.1.2.0) using settings of 7% minimum overlap, 3% maximum shift and Best/Best for the Comparer/Optimizer. No image enhancing processing was performed for individual tiles. Using ImageJ (National Institutes of Health, Bethesda, Md.) individual cell fluorescence intensities were measured by first segmenting the 8-bit tiff image for the 6/CFSE/FNHS channel by manually finding the minimum intensity below which object boundaries began to expand into the background (the built-in watershed algorithm was also utilized to separate touching objects). Using a histogram of object sizes, the minimal object area was chosen and pixel intensity for each of those objects were recorded. This process was carried out for 3 separate plates of cells.

Example 7

Fixed Cell Imaging

One day prior to imaging, NIH 3T3 cells were seeded at 20,000 cells per well in a 24-well plate (Corning Costar, TC-treated). After 24 hours of incubation (37° C., 5% CO$_2$), the media was removed from the plate and cells were washed twice with DPBS (Ca and Mg free, Life Sciences). A total of 300 μL of 4% paraformaldehyde in DPBS was added to each well and incubated at room temperature for one hour. The paraformaldehyde was removed and the cells were washed with DPBS three times. For experiments with permeabilized cells, 300 μL of 0.1% Triton X-100 was added to each well, allowed to sit for 10 minutes at room temperature, and then washed twice with DPBS. Otherwise, the fixed cells were used immediately. A total of 320 μL of DPBS was added to each well, and then 40 μL of Hoechst 33342 (final concentration of 0.5 μg/mL) and 40 μL of 4 (final concentrations from 10 μM to 1 nM were tested, final DMSO concentration=0.1%) or 5-(6-)carboxyfluorescein succinimidyl ester (FNHS, final concentrations from 10 μM to 1 nM were tested, final DMSO concentration=0.1%). Cells were incubated (room temperature) for 30 minutes, then rinsed one time with DPBS (Ca and Mg free, Life Sciences) and 500 μL of DPBS was added to each well. Cells were then imaged using a total of 20 tiles per well with a 20% overlap. Each tile included 3 channel acquisitions: phase contrast, Hoechst 33342, 4/CFSE/FNHS (Zeiss F38 filter, 470 nm LED @100% power, at either 200-ms or 1000-ms exposure). Images were stitched using the Hoechst channel as the reference channel with Zen 2012 (V1.1.2.0) using settings of 7% minimum overlap, 3% maximum shift and Best/Best for the Comparer/Optimizer. No image enhancing processing was performed for individual tiles. Using ImageJ (National Institutes of Health, Bethesda, Md.) individual cell fluorescence intensities were measured by first segmenting the 8-bit tiff image for the 4/CFSE/FNHS channel by manually finding the minimum intensity below which object boundaries began to expand into the background (the built-in watershed algorithm was also utilized to separate touching objects). Using a histogram of object sizes, the minimal object area was chosen and pixel intensity for each of those objects were recorded. This process was carried out for 3 separate plates of cells.

Example 8

Cell Viability Studies

On day one, 5,000 cells per well were plated on a clear 96-well plate (Corning Costar, TC-treated) along with several blank wells with media only. The next day, the media was replaced with 180 μL of DPBS with glucose and 20 μL of 4 (final concentrations from 30 μM to 1 nM were tested, final DMSO concentration=0.1%) and incubated for 30 minutes. The dye solution was removed from the wells and 200 μL of fresh media was added to each well in the plate. The plate was then incubated (37° C., 5% CO$_2$) for 72 hours. Then 40 μL of MTS (Promega, CellTiter 96® AQ$_{ueous}$ One Solution Cell Proliferation Assay) was added to each well and the plate was incubated (37° C., 5% CO$_2$) for 4 hours. The absorbance of each well at 540 nm was measured on a Synergy HT plate reader (BioTek Instruments, Inc.). All assays were performed in triplicate on three separate plates.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances.

It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A process for making an asymmetric fluorophore, the process comprising:

decarboxylating a compound of Formula 1

Formula 1

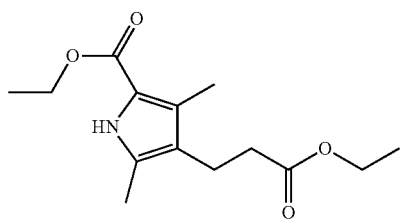

to form a compound of Formula 2

Formula 2

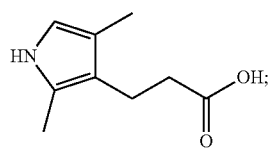

condensing the compound of Formula 2 with 2-pyrrole aldehyde to form a compound of Formula 3

Formula 3

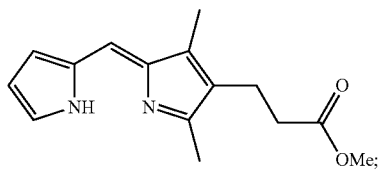

difluorinating the compound of Formula 3 in a presence of boron trifluoride ethyl etherate to form a compound of Formula 4

Formula 4

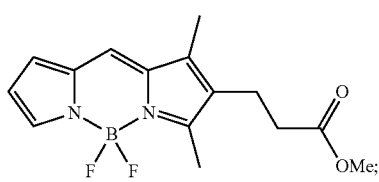

hydrolyzing the compound of Formula 4 to form a compound of Formula 5

Formula 5

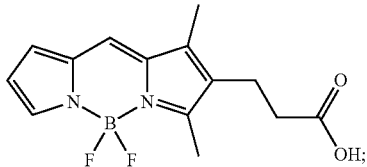

and succinimating the compound of Formula 5 to form the asymmetric fluorophore Formula 6

Formula 6

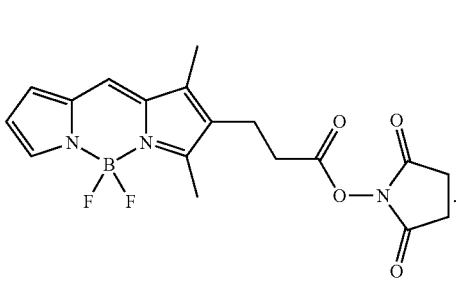

2. The process for making the asymmetric fluorophore of claim 1, wherein decarboxylating the compound of Formula 1 comprises combining the compound of Formula 1 with phosphoric acid.

3. The process for making the asymmetric fluorophore of claim 2, further comprising performing the decarboxylation at a temperature from 75° C. to 100° C.

4. The process for making the asymmetric fluorophore of claim 1, wherein condensing the compound of Formula 2 occurs in a presence of $POCl_3$.

5. The process for making the asymmetric fluorophore of claim 1, wherein difluorinating the compound of Formula 3 occurs in a presence of di-isopropylethylamine.

6. The process for making the asymmetric fluorophore of claim 1, wherein hydrolyzing the compound of Formula 4 occurs in a presence of hydrochloric acid.

7. The process for making the asymmetric fluorophore of claim 1, wherein succinimating the compound of Formula 5 comprises coupling the compound of Formula 5 with N-hydroxysuccinimide.

* * * * *